(12) United States Patent
Min et al.

(10) Patent No.: US 11,000,383 B2
(45) Date of Patent: May 11, 2021

(54) DEVICE FOR SUPPORTING HOOP STRESS OF MENISCUS

(71) Applicant: AJOU UNIVERSITY INDUSTRY-ACADEMIC COOPERATION FOUNDATION, Suwon-si (KR)

(72) Inventors: Byoung Hyun Min, Seoul (KR); Young Jick Kim, Suwon-si (KR); Xiang Yun Yin, Suwon-si (KR); Do Young Park, Suwon-si (KR)

(73) Assignee: AJOU UNIVERSITY INDUSTRY-ACADEMIC COOPERATION FOUNDATION, Suwon-si (KR)

( * ) Notice: Subject to any disclaimer, the term of this patent is extended or adjusted under 35 U.S.C. 154(b) by 32 days.

(21) Appl. No.: 16/376,133

(22) Filed: Apr. 5, 2019

(65) Prior Publication Data

US 2019/0290443 A1 Sep. 26, 2019

Related U.S. Application Data

(63) Continuation of application No. PCT/KR2017/010946, filed on Sep. 29, 2017.

(30) Foreign Application Priority Data

Oct. 6, 2016 (KR) .......................... 10-2016-0129065

(51) Int. Cl.
*A61F 2/38* (2006.01)
*A61B 17/56* (2006.01)
(Continued)

(52) U.S. Cl.
CPC ............ *A61F 2/3872* (2013.01); *A61B 17/00* (2013.01); *A61B 17/56* (2013.01); *A61F 2002/30014* (2013.01); *A61F 2002/30462* (2013.01)

(58) Field of Classification Search
CPC ........ A61F 2/30756; A61F 2002/30766; A61F 2/3872; A61F 2002/30014;
(Continued)

(56) References Cited

U.S. PATENT DOCUMENTS 4,344,193 A * 8/1982 Kenny .................. A61F 2/3872
128/DIG. 21
4,502,161 A * 3/1985 Wall ...................... A61F 2/3872
623/14.12
(Continued)

FOREIGN PATENT DOCUMENTS

KR 10-2014-0029483 A 3/2014
WO 2012/159018 A1 11/2012
(Continued)

OTHER PUBLICATIONS

International Search Report for PCT/KR2017/010946 dated Feb. 19, 2018 (PCT/ISA/210).

*Primary Examiner* — Alvin J Stewart
(74) *Attorney, Agent, or Firm* — Sughrue Mion, PLLC (57) ABSTRACT

Disclosed is a device for supporting hoop stress applied to a meniscus and preventing deviation of the meniscus, and the device for supporting hoop stress applied to a meniscus and preventing deviation of the meniscus may include an intermediate support member, one side extension member, and the other side extension member.

12 Claims, 8 Drawing Sheets

(51) Int. Cl.
*A61B 17/00* (2006.01)
*A61F 2/30* (2006.01)

(58) Field of Classification Search
CPC ....... A61F 2002/30462; A61B 17/0401; A61B 17/04; A61B 17/0469; A61B 17/06; A61B 17/06004; A61B 17/06166; A61B 2017/0485; A61B 17/0487; A61B 17/0495
See application file for complete search history.

(56) References Cited

U.S. PATENT DOCUMENTS

| | | | | |
|---|---|---|---|---|
| 4,919,667 A * | 4/1990 | Richmond | A61F 2/3872 | 623/14.12 |
| 5,092,894 A * | 3/1992 | Kenny | A61F 2/3872 | 128/898 |
| 5,171,322 A * | 12/1992 | Kenny | A61F 2/3872 | 623/14.12 |
| 5,855,619 A * | 1/1999 | Caplan | A61B 17/1146 | 623/23.72 |
| 5,972,022 A * | 10/1999 | Huxel | A61B 17/0401 | 606/215 |
| 5,989,256 A * | 11/1999 | Kuslich | A61B 17/7022 | 606/103 |
| 6,371,990 B1 * | 4/2002 | Ferree | A61F 2/441 | 623/17.16 |
| 6,425,919 B1 * | 7/2002 | Lambrecht | A61F 2/441 | 623/17.16 |
| 6,579,291 B1 * | 6/2003 | Keith | A61B 17/70 | 128/898 |
| 6,712,853 B2 * | 3/2004 | Kuslich | A61F 2/4601 | 623/17.16 |
| 6,736,815 B2 * | 5/2004 | Ginn | A61F 2/4611 | 606/246 |
| 6,805,695 B2 * | 10/2004 | Keith | A61B 17/8897 | 623/17.11 |
| 6,911,003 B2 * | 6/2005 | Anderson | A61B 17/0401 | 600/30 |
| 7,048,682 B2 * | 5/2006 | Neisz | A61B 17/0487 | 600/30 |
| 7,163,563 B2 * | 1/2007 | Schwartz | A61B 17/064 | 623/14.12 |
| 7,344,539 B2 * | 3/2008 | Serhan | A61F 2/0811 | 623/13.11 |
| 7,524,333 B2 * | 4/2009 | Lambrecht | A61B 17/70 | 606/246 |
| 7,799,060 B2 * | 9/2010 | Lange | A61B 17/7022 | 606/257 |
| 7,828,850 B2 * | 11/2010 | Cauthen, III | A61F 2/442 | 623/17.16 |
| 7,857,857 B2 * | 12/2010 | Kim | A61F 2/442 | 623/17.11 |
| 7,959,679 B2 * | 6/2011 | Lambrecht | A61B 5/1076 | 623/17.11 |
| 8,118,834 B1 * | 2/2012 | Goraltchouk | A61B 17/06166 | 606/228 |
| 8,163,022 B2 * | 4/2012 | Bentley | A61B 17/0487 | 623/17.11 |
| 8,287,594 B2 * | 10/2012 | Cragg | A61F 2/3872 | 623/14.12 |
| 8,292,954 B2 * | 10/2012 | Robinson | A61F 2/4606 | 623/14.12 |
| 8,357,203 B2 * | 1/2013 | White | A61B 17/562 | 623/14.12 |
| 8,623,085 B2 * | 1/2014 | Gatt | A61F 2/30756 | 623/14.12 |
| 8,771,353 B2 * | 7/2014 | Gedet | A61F 2/3872 | 623/14.12 |
| 8,814,902 B2 * | 8/2014 | Bonutti | A61B 17/0401 | 606/232 |
| 8,845,639 B2 * | 9/2014 | Wallace | A61B 17/32002 | 606/85 |
| 9,044,225 B1 * | 6/2015 | Goraltchouk | A61B 17/06166 | |
| 9,144,483 B2 * | 9/2015 | Chu | A61B 17/0401 | |
| 9,498,335 B2 * | 11/2016 | McCullen | A61F 2/3872 | |
| 9,532,777 B2 * | 1/2017 | Kaiser | A61F 2/0811 | |
| 9,655,730 B2 * | 5/2017 | Fox | A61F 2/3872 | |
| 9,724,086 B2 * | 8/2017 | Marathakis | A61B 17/06004 | |
| 9,913,710 B2 * | 3/2018 | Perriello | A61F 2/0811 | |
| 10,022,230 B2 * | 7/2018 | Amis | A61F 2/30756 | |
| 10,034,755 B2 * | 7/2018 | McCullen | A61F 2/30767 | |
| 10,626,521 B2 * | 4/2020 | Rizk | A61L 31/148 | |
| 10,695,045 B2 * | 6/2020 | Kaiser | A61B 17/0401 | |
| 2002/0077661 A1 * | 6/2002 | Saadat | A61F 2/30756 | 606/221 |
| 2002/0077701 A1 * | 6/2002 | Kuslich | A61F 2/442 | 623/17.12 |
| 2002/0120270 A1 * | 8/2002 | Trieu | A61B 17/7022 | 623/13.11 |
| 2002/0143329 A1 * | 10/2002 | Serhan | A61B 17/0642 | 623/13.11 |
| 2003/0040796 A1 * | 2/2003 | Ferree | A61F 2/441 | 623/17.11 |
| 2003/0045937 A1 * | 3/2003 | Ginn | A61F 2/4611 | 623/17.11 |
| 2003/0078579 A1 * | 4/2003 | Ferree | A61F 2/442 | 606/53 |
| 2004/0002763 A1 * | 1/2004 | Phillips | A61B 17/0401 | 623/17.16 |
| 2004/0039392 A1 * | 2/2004 | Trieu | A61F 2/442 | 606/86 R |
| 2004/0097927 A1 * | 5/2004 | Yeung | A61B 17/70 | 606/86 A |
| 2004/0097980 A1 * | 5/2004 | Ferree | A61F 2/4611 | 606/151 |
| 2004/0143344 A1 * | 7/2004 | Malaviya | A61L 27/18 | 623/23.72 |
| 2005/0159817 A1 * | 7/2005 | Ferree | A61B 17/15 | 623/17.11 |
| 2006/0089646 A1 * | 4/2006 | Bonutti | A61F 2/0811 | 606/279 |
| 2007/0027471 A1 * | 2/2007 | Ferree | A61F 2/30742 | 606/213 |
| 2007/0100450 A1 * | 5/2007 | Hodorek | A61L 27/52 | 623/14.12 |
| 2008/0221686 A1 * | 9/2008 | Ferree | A61F 2/442 | 623/17.11 |
| 2008/0255665 A1 * | 10/2008 | Weissberg | A61F 2/3872 | 623/14.12 |
| 2009/0012540 A1 * | 1/2009 | Ferguson | A61F 2/442 | 606/151 |
| 2009/0024165 A1 * | 1/2009 | Ferree | A61B 17/7053 | 606/246 |
| 2010/0087926 A1 * | 4/2010 | Butler | A61F 2/442 | 623/17.16 |
| 2011/0093073 A1 * | 4/2011 | Gatt | A61F 2/3872 | 623/14.12 |
| 2012/0095468 A1 * | 4/2012 | Wallace | A61B 17/864 | 606/79 |
| 2012/0232656 A1 * | 9/2012 | Gedet | A61F 2/3872 | 623/14.12 |
| 2013/0079877 A1 * | 3/2013 | Buma | A61F 2/3872 | 623/14.12 |
| 2013/0190815 A1 * | 7/2013 | Mansmann | A61F 2/30756 | 606/232 |
| 2014/0222149 A1 * | 8/2014 | Amis | A61F 2/3872 | 623/14.12 |
| 2015/0238318 A1 * | 8/2015 | McCullen | A61F 2/3872 | 623/14.12 |
| 2016/0256285 A1 * | 9/2016 | Jansen | A61L 27/165 | |
| 2017/0056180 A1 * | 3/2017 | Schmieding | A61F 2/4644 | |
| 2017/0128215 A1 * | 5/2017 | Denham | A61F 2/3094 | |
| 2017/0224498 A1 * | 8/2017 | McCullen | A61F 2/30767 | |
| 2017/0333101 A1 * | 11/2017 | Zeetser | A61B 17/842 | |
| 2018/0360610 A1 * | 12/2018 | Patel | A61F 2/442 | |
| 2019/0307441 A1 * | 10/2019 | Lombardo | A61B 17/0401 | |
| 2020/0060834 A1 * | 2/2020 | McCullen | A61F 2/3872 | |

(56) References Cited

U.S. PATENT DOCUMENTS

| | | | |
|---|---|---|---|
| 2020/0146809 A1* | 5/2020 | Petros | A61F 2/0811 |
| 2020/0178954 A1* | 6/2020 | Burkhart | A61B 17/0401 |
| 2020/0197145 A1* | 6/2020 | Morningstar | A61F 2/0045 |

FOREIGN PATENT DOCUMENTS

| | | |
|---|---|---|
| WO | 2014/053800 A1 | 4/2014 |
| WO | 2016/054463 A1 | 4/2016 |

\* cited by examiner

(a) MENISCUS AT EXACT POSITION (b) DEVIATED MENISCUS

DEVICE FOR SUPPORTING HOOP STRESS OF MENISCUS

TECHNICAL FIELD

The present invention relates to a device for supporting hoop stress applied to a meniscus.

BACKGROUND ART

Meniscus are C-shaped or circular fibrocartilages located at the periphery of joints between articular surfaces of femora and tibiae in the knees. In general, the meniscus is torn by acute trauma in the case of younger patients, while the meniscus is torn commonly by degenerative changes in older patients. When the meniscus is injured, the torn tissue may move and impinged in an abnormal manner in the joint, which causes pain and wear of the articular cartilage and results in a loss of a function of the joint.

Figure 1:
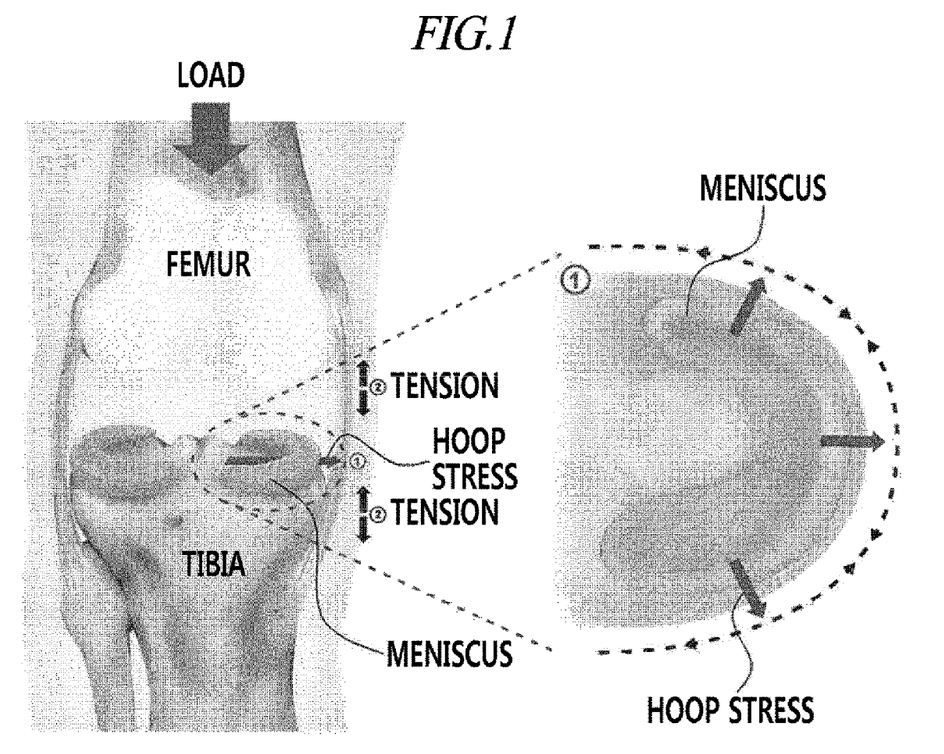
FIG. 1 is a conceptual view illustrating an influence of hoop stress applied to a meniscus.

If the meniscus is torn or a function of the meniscus maintaining annular tension is lost due to the degenerative change, the torn meniscus deviates from a normal position and thus extrudes out of an articular surface, which causes a reduction in ability of the meniscus absorbing impact and results in injuries to articular cartilages. Specifically, hoop stress is applied to the meniscus positioned between the femur and the tibia when a load is transmitted to the femur (see FIG. 1). For this reason, the meniscus existing at an normal anatomical position deviates from the its exact position and applies a pressure on a medial collateral ligament (MCL) and surrounding capsule (see FIG. 2). In some instances, it is possible to restore the torn or deviated meniscus. The restoration of the meniscus may be performed by arthroscopic surgery, but the surgical restoration using sutures is very difficult because it is difficult to compress and fix a torn surface, and as a result, there is a limitation in that the surgical restoration causes a permanent change in position of the meniscus.

Korean Patent Application Laid-Open No. 10-2014-0029483 discloses a device for suturing a torn meniscus and a surgical method, but the device and the method are related to a technology for restoring the already torn or deviated meniscus and has a problem in that there occurs a permanent change in position of the meniscus.

Therefore, there is a need for a device and/or a method of preventing the meniscus from deviating from the exact position instead of restoring the already torn or deviated meniscus.

DISCLOSURE

Technical Problem

The present invention has been made in an effort to solve the above-mentioned problems in the related art, and an object of the present invention is to provide a device for preventing deviation of a meniscus or restoring the meniscus by supporting hoop tension of the meniscus.

Technical problems to be solved by the present invention are not limited to the above-mentioned technical problems, and other technical problems, which are not mentioned above, may be clearly understood by those skilled in the art from the following descriptions.

Technical Solution

A first aspect of the present invention, as a technical means for solving the above-mentioned technical problem, provides a device for supporting hoop stress applied to a meniscus and preventing deviation of the meniscus, the device including: an intermediate support member which surrounds the meniscus to support the hoop stress applied to the meniscus; one side extension member which is connected to one end of the intermediate support member and fixed to a lateral surface of a tibia through one side tunnel that extends laterally from an upper surface of the tibia positioned below the meniscus; and the other side extension member which is connected to the other end of the intermediate support member and fixed to the lateral surface of the tibia through the other side tunnel that extends laterally from the upper surface of the tibia.

Advantageous Effects

According to the technical solution, the device may be fixedly disposed to surround the meniscus in order to support hoop stress applied to the meniscus, and as a result, it is possible to prevent deviation of the meniscus caused by the hoop stress applied to the meniscus, and thus it is possible to prevent degenerative arthritis caused by the deviation of the meniscus.

DESCRIPTION OF MAIN REFERENCE NUMERALS OF DRAWINGS

100: Device for supporting hoop stress applied to meniscus and preventing deviation of meniscus
110a: Rigid member
110b: Elastic member
110: Intermediate support member
120: One side extension member
130: The other side extension member
140: Fixing unit
210: Medial meniscus
211: Annular fiber arrangement portion
212: Radial fiber arrangement portion
213: Network fiber arrangement portion
220: Lateral meniscus
221: Annular fiber arrangement portion 222: Radial fiber arrangement portion
223: Network fiber arrangement portion
300: Tibia
310: One side tunnel
320: The other side tunnel
410: Posterior cruciate ligament
420: Anterior cruciate ligament

BEST MODE

Hereinafter, exemplary embodiments of the present invention will be described in detail with reference to the accompanying drawings so that those with ordinary skill in the art to which the present invention pertains may easily carry out the exemplary embodiments.

However, the present invention may be implemented in various different ways and is not limited to the exemplary embodiments described herein. A part irrelevant to the description will be omitted in the drawings in order to clearly describe the present invention, and similar constituent elements will be designated by similar reference numerals throughout the specification.

Throughout the specification, when one constituent element is referred to as being "connected to" another constituent element, one constituent element can be "directly connected to" the other constituent element, and one constituent element can also be "electrically connected to" the other element with other elements therebetween.

Throughout the specification, when one member is disposed "on" another member in the present specification, this includes not only a case where the one member is brought into contact with another member, but also a case where still another member is present between the two members.

Throughout the specification, unless explicitly described to the contrary, the word "comprise" or "include" and variations, such as "comprises", "comprising", "includes" or "including", will be understood to imply the inclusion of stated constituent elements, not the exclusion of any other constituent elements.

Words of degree, such as "about", "substantially", and the like are used in the present specification in the sense of "at, or nearly at, when given the manufacturing, design, and material tolerances inherent in the stated circumstances" and are used to prevent the unscrupulous infringer from unfairly taking advantage of the invention disclosure where exact or absolute figures and operational or structural relationships are stated as an aid to understanding the invention. In addition, throughout the specification, the term "step of" does not mean "step for".

Throughout the specification, the term "combination(s) of" included in Markush type description means mixture or combination of one or more constituent elements selected from a group consisting of constituent elements described in Markush type and thus means that the disclosure includes one or more constituent elements selected from the Markush group.

Throughout the specification, a phrase in the form "A and/or B" means "A or B, or A and B".

Hereinafter, a device for supporting hoop stress applied to a meniscus and preventing deviation of the meniscus according to the present invention will be specifically described with reference to the exemplary embodiments and the drawings. However, the present invention is not limited to the exemplary embodiments and the drawings.

A first aspect of the present invention provides a device for supporting hoop stress applied to a meniscus and preventing deviation of the meniscus, the device including: an intermediate support member which surrounds the meniscus to support hoop stress applied to the meniscus; one side extension member which is connected to one end of the intermediate support member and fixed to a lateral surface of a tibia through one side tunnel that extends laterally from an upper surface of the tibia positioned below the meniscus; and the other side extension member which is connected to the other end of the intermediate support member and fixed to the lateral surface of the tibia through the other side tunnel that extends laterally from the upper surface of the tibia.

Figure 3:
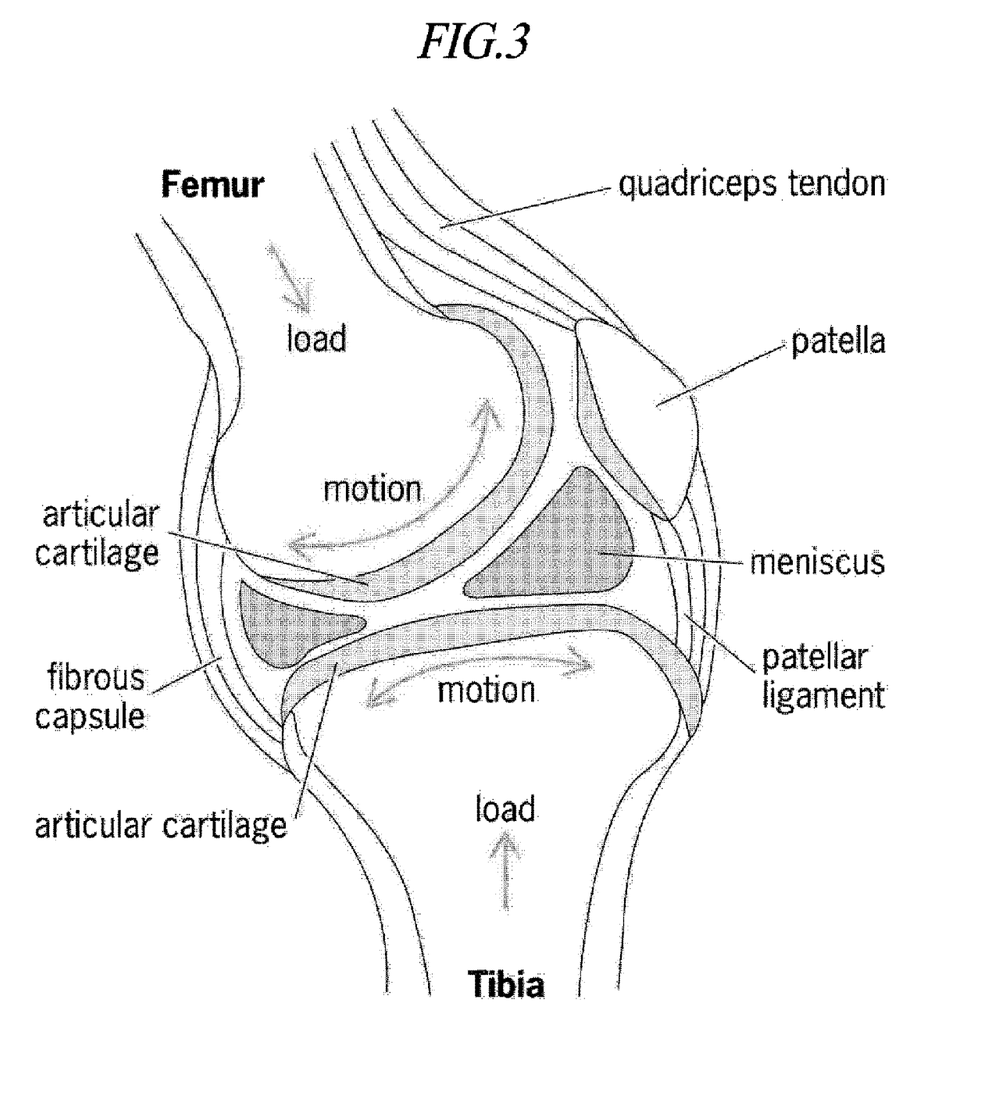
FIG. 3 is a conceptual view for explaining a structure of a knee joint including a meniscus.
Figure 4A:
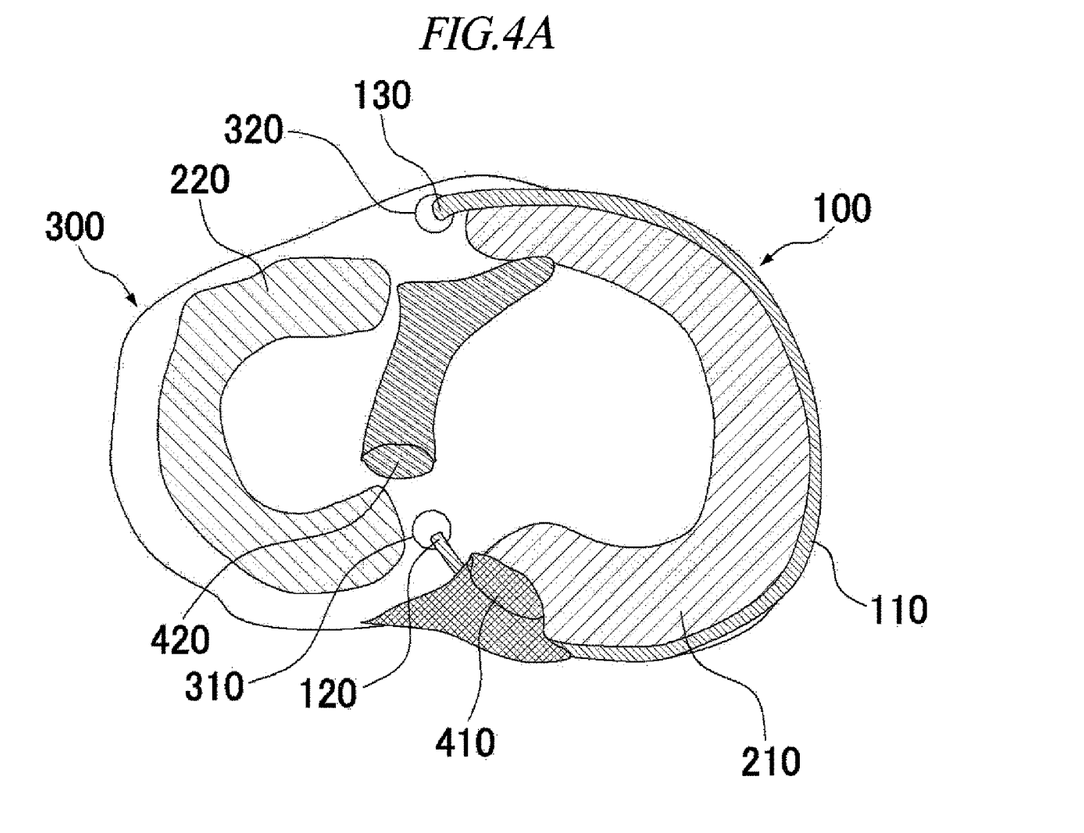
FIGS. 4A and 4B are schematic top plan and side views for explaining a device for supporting hoop stress applied to a meniscus and preventing deviation of the meniscus according to an exemplary embodiment of the present invention which is disposed in a knee joint.
Figure 4B:
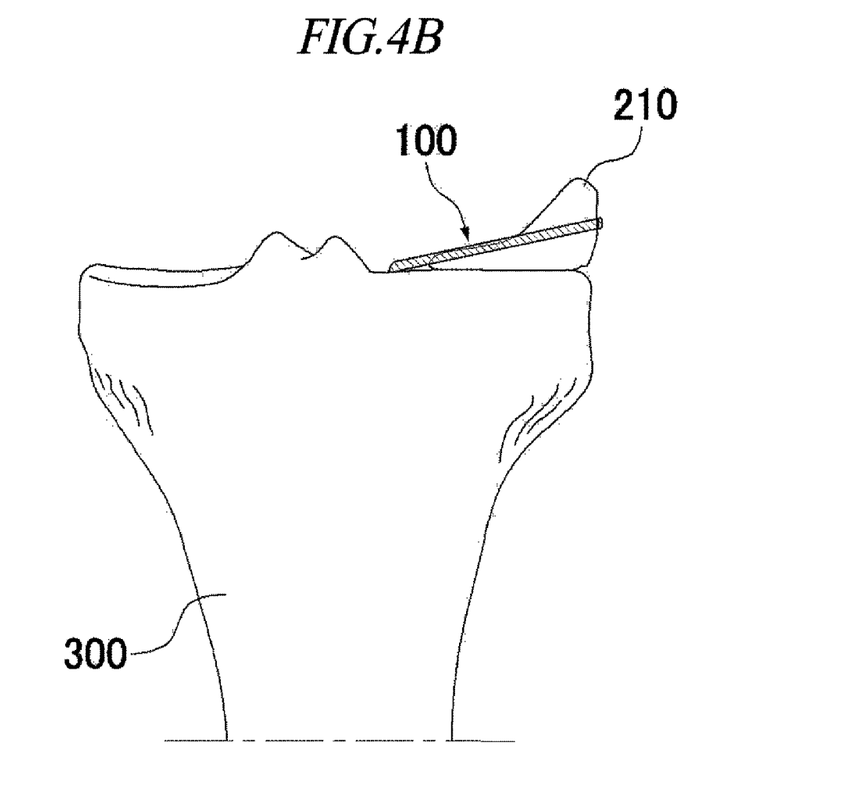

FIG. 3 is a conceptual view for explaining a structure of a knee joint including a meniscus, and FIGS. 4A and 4B are schematic top plan and side views for explaining the device for supporting hoop stress applied to a meniscus and preventing deviation of the meniscus according to the exemplary embodiment of the present invention. In addition, FIG. 5 is a schematic stereoscopic view for explaining the device for supporting hoop stress applied to a meniscus and preventing deviation of the meniscus according to the exemplary embodiment of the present invention which is disposed in the knee joint.

Figure 5:
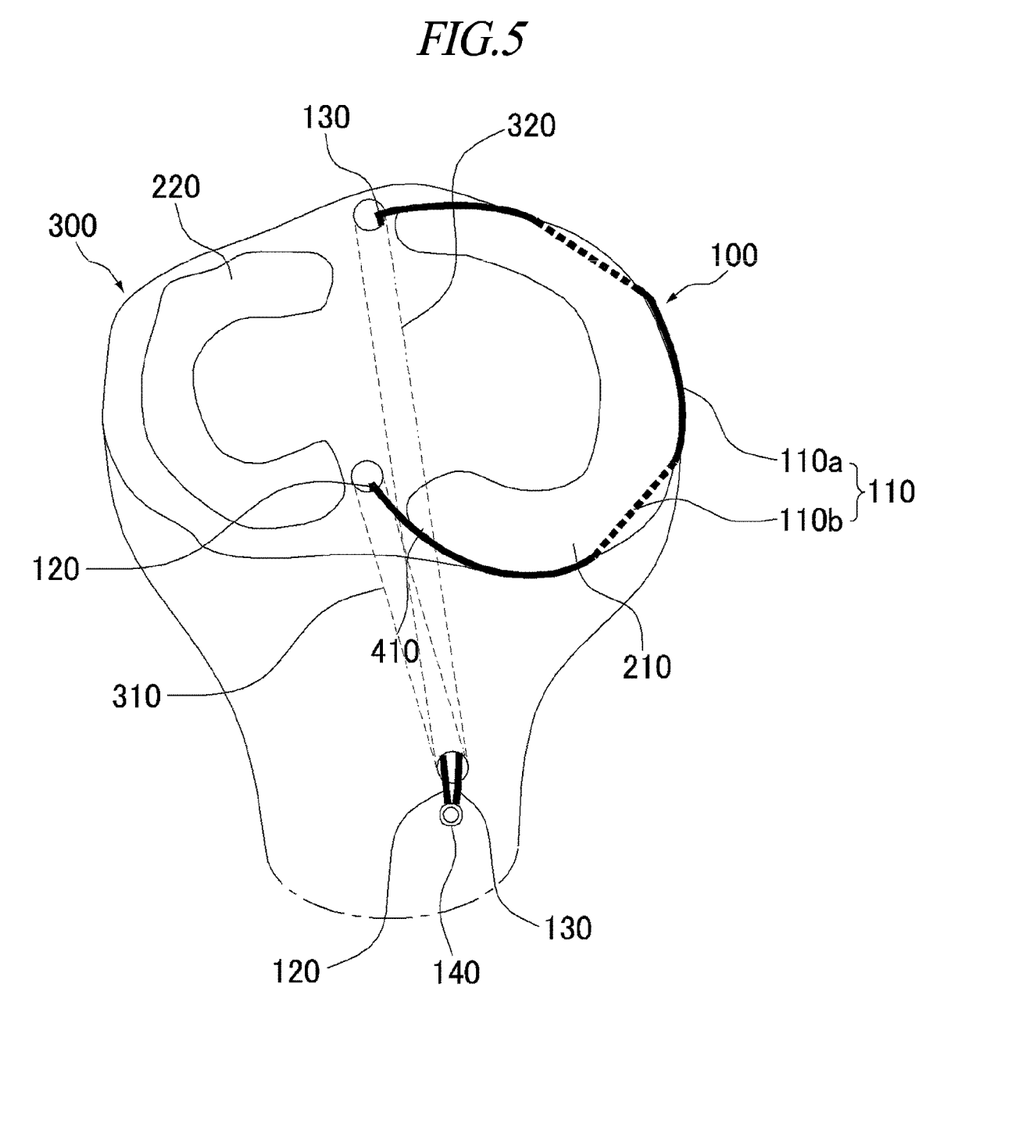
FIG. 5 is a schematic stereoscopic view for explaining the device for supporting hoop stress applied to a meniscus and preventing deviation of the meniscus according to the exemplary embodiment of the present invention which is disposed in the knee joint.

Referring to FIGS. 4A, 4B, and 5, the device 100 for supporting hoop stress applied to a meniscus and preventing deviation of the meniscus includes an intermediate support member 110.

The intermediate support member 110 is configured to surround the meniscus to support hoop stress applied to the meniscus.

In this case, it should not be interpreted that the configuration in which the intermediate support member 110 surrounds the meniscus is limited only to a configuration in which the intermediate support member 110 surrounds an outermost side of the meniscus. In other words, the configuration in which the intermediate support member 110 surrounds the meniscus may be widely interpreted as including a concept in which the intermediate support member 110 passes through an inner part disposed inward from the outermost side of the meniscus and surrounds a portion disposed inward from the inner part through which the intermediate support member 110 passes. The exemplary embodiment related to this configuration will be described below with reference to FIG. 5. In addition, the meniscus surrounded by the intermediate support member 110 may be, but not limited only to, a medial meniscus 210 as illustrated in FIGS. 4A, 4B, and 5. That is, the intermediate support member 110 may surround the medial meniscus 210 or a lateral meniscus 220. However, hereinafter, the meniscus will be denoted by reference numeral 210 for convenience of description.

Figure 2:
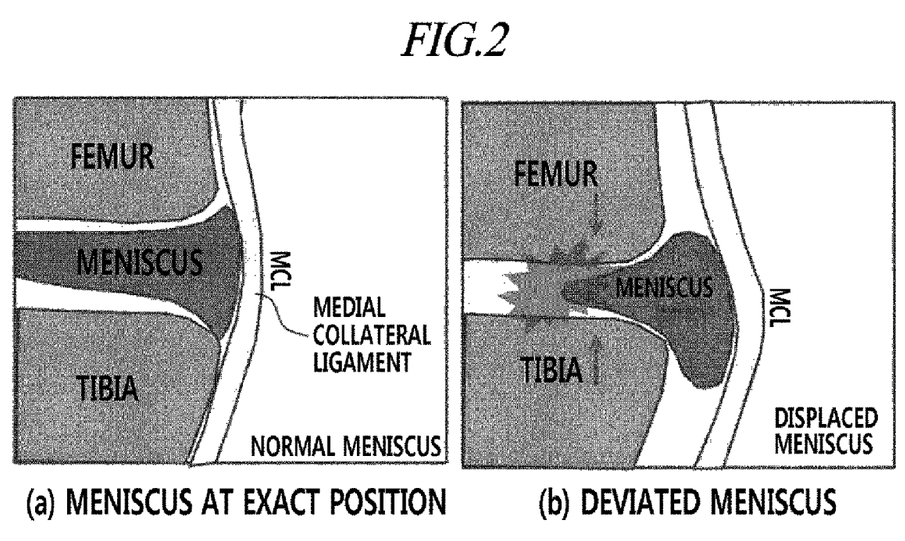
FIG. 2 is a conceptual view for explaining a state in which a meniscus deviates from an exact position by hoop stress.

The intermediate support member 110 may prevent the meniscus from deviating from an exact position (see (b) of FIG. FIG. 2) due to hoop stress (see FIG. 1) applied to the meniscus.

According to the exemplary embodiment of the present invention, the intermediate support member 110 may surround a part of an outer circumferential surface of the meniscus 210, as illustrated in FIGS. 4A, 4B, and 5. In addition, the intermediate support member 110 may be configured to pass through a part of an inner portion of a joint capsule outside the meniscus 210. The intermediate support member 110 may extend while alternately passing through the inner and outer portions of the joint capsule outside the meniscus 210 at least once (particularly, two or three times). As an example, as illustrated in FIG. 5, a portion of the intermediate support member 110, which is indicated by reference numeral 110a, is a portion that extends along the outer portion of the joint capsule outside the meniscus 210, and a portion of the intermediate support member 110, which is indicated by reference numeral 110b, is a portion that extends along the inner portion of the joint capsule outside the meniscus 210.

As described above, the intermediate support member 110 may be disposed as one end of one side extension member 120 moves and passes alternately through the inner and outer portions of the joint capsule outside the meniscus 210 at least once and then moves out of the meniscus 210. This configuration may be understood as a concept similar to a stitch. With this configuration, coupling force between the intermediate support member 110 and the meniscus 210 may be improved. As an example, a surgical robot or a practitioner may repeat, several times, a process of moving the one end of the one side extension member 120 along the outer portion of the joint capsule by a predetermined distance, inserting the one end of the one side extension member 120 into the inner portion (interior) of the joint capsule, moving the one end of the one side extension member 120 in a circumferential direction by a predetermined distance, and then drawing the one end of the one side extension member 120 to the outer portion (exterior) of the joint capsule, and then the surgical robot or the practitioner may move the one side extension member 120 until the intermediate support member 110, which is continuously connected to the one side extension member 120, is positioned to surround the meniscus 210 (see FIG. 5).

Figure 6:
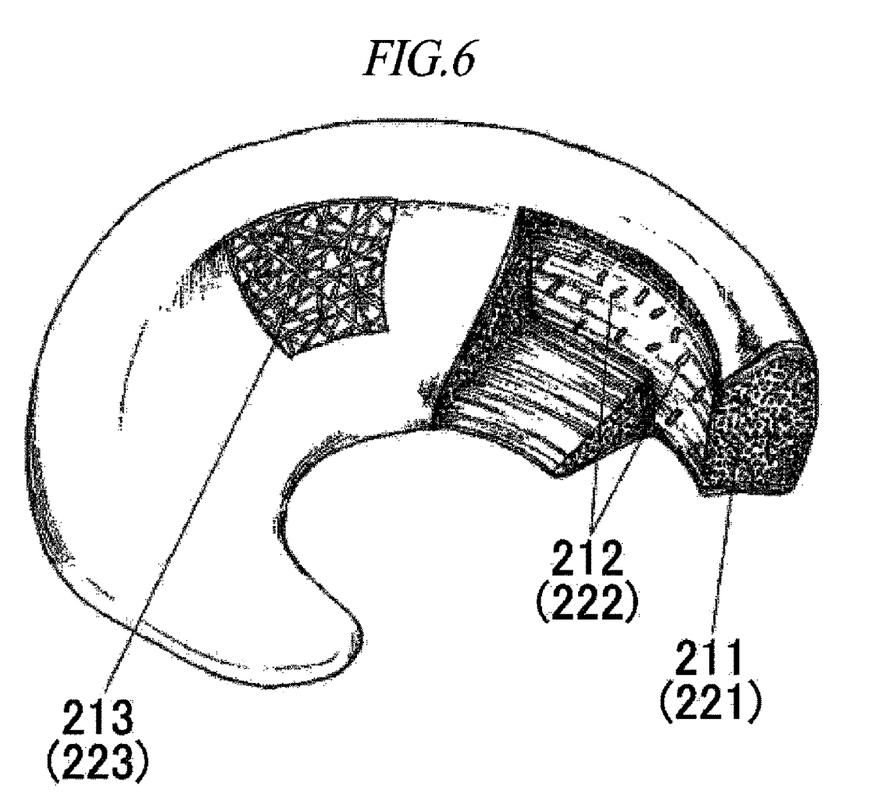
FIG. 6 is a conceptual view for explaining a structure of the meniscus.

Meanwhile, FIG. 6 is a conceptual view for explaining a structure of a meniscus.

Referring to FIG. 6, the menisci 210 and 220 include annular fiber arrangement portions 211 and 221 and radial fiber arrangement portions 212 and 222. In addition, the menisci may include network fiber arrangement portions 213 and 223. According to the exemplary embodiment of the present invention, the intermediate support member 110 may pass through one or both of the inner and outer portions of the joint capsule that surrounds an outer portion (outer circumference) of the annular fiber arrangement portion which is a portion positioned at an outermost side among sub-portions of the meniscus (see FIGS. 5 and 6). In other words, the intermediate support member 110 may be disposed to be in contact with one or both of the inner and outer portions of the joint capsule outside the meniscus.

Since the intermediate support member 110 extends while passing alternately through the inner and outer portions of the joint capsule outside the meniscus 210 at least once, the intermediate support member 110 may fixedly and integrally surround the meniscus 210, such that it is possible to stably and basically support hoop stress applied to the meniscus 210 with higher reliability, and it is possible to more effectively prevent the outward deviation of the meniscus 210.

Referring to FIGS. 4A, 4B, and 5, the device 100 for supporting hoop stress applied to a meniscus and preventing deviation of the meniscus includes the one side extension member 120.

The one side extension member 120 is connected to the one end of the intermediate support member 110 and fixed to a lateral surface of a tibia 300 through one side tunnel 310 that extends laterally from an upper surface of the tibia 300 positioned below the meniscus 210.

The one side extension member 120 may be continuously connected to the intermediate support member 110. As an example, the intermediate support member 110, the one side extension member 120, and the other side extension member 130 may be made of the same material and configured integrally and continuously. In addition, referring to FIG. 5, the one side tunnel 310 may have an upper opening formed in the upper surface of the tibia 300 and a lateral opening formed in the lateral surface of the tibia 300. The one side tunnel 310 may be formed by using various medical instruments (including typical medical instruments and new medical instruments to be released in the future) such as an ultra-small drilling device which a surgical robot or a practitioner may use to form a tunnel (hole) having a small diameter in a bone. As an example, referring to FIG. 5, the one end of the one side extension member 120 may be exposed from the lateral surface of the tibia 300 through the lateral opening of the one side tunnel 310, and the other end of the one side extension member 120 may be connected to the one end of the intermediate support member 110 on the upper surface of the tibia 300 through the upper opening of the one side tunnel 310.

In addition, referring to FIG. 5, the upper opening of the one side tunnel 310 may be formed adjacent to one end of the meniscus 210. More specifically, the upper opening of the one side tunnel 310 may be formed adjacent to the one end of the meniscus 210 so that predetermined tension is applied to the intermediate support member 110 to enable the intermediate support member 110 to tensely surround the meniscus 210 when the one end of the one side extension member 120 exposed through the lateral opening of the one side tunnel 310 and the other end of the other side extension member 130 exposed through a lateral opening of the other side tunnel 320 are pulled by predetermined force.

In addition, the one end of the one side extension member 120 may be inserted through the lateral opening of the other side tunnel 320, moved to an upper opening of the other side tunnel 320, moved to pass through the meniscus 210 while surrounding the meniscus 210, inserted into the one side tunnel 310 through the upper opening of the one side tunnel 310, exposed through the lateral opening of the one side tunnel 310, and then fixed to the lateral surface of the tibia 300.

In addition, referring to FIG. 5, the intermediate support member 110 may be disposed to surround the meniscus 210 when the one side extension member 120 is inserted through the upper opening of the one side tunnel 310 and then the one end of the one side extension member 120 is moved to be exposed through the lateral opening of the one side tunnel 310.

Referring to FIGS. 4A, 4B, and 5, the device 100 for supporting hoop stress applied to a meniscus and preventing deviation of the meniscus includes the other side extension member 130.

The other side extension member 130 is connected to the other end of the intermediate support member 110 and fixed to the lateral surface of the tibia 300 through the other side tunnel 320 that extends laterally from the upper surface of the tibia 300.

The other side extension member 130 may be continuously connected to the intermediate support member 110. In addition, referring to FIG. 5, the other side tunnel 320 may have the upper opening formed in the upper surface of the tibia 300 and the lateral opening formed in the lateral surface of the tibia 300. The other side tunnel 320 may be formed in the same or similar manner as the one side tunnel 320. As an example, referring to FIG. 5, the other end of the other side extension member 130 may be exposed from the lateral surface of the tibia 300 through the lateral opening of the other side tunnel 310, and one end of the other side extension member 130 may be connected to the other end of the intermediate support member 110 on the upper surface of the tibia 300 through the upper opening of the other side tunnel 320.

In addition, referring to FIG. 5, the upper opening of the other side tunnel 310 may be formed adjacent to the other end of the meniscus 210. More specifically, the upper opening of the other side tunnel 320 may be formed adjacent to the other end of the meniscus 210 so that predetermined tension is applied to the intermediate support member 110 to enable the intermediate support member 110 to tensely surround the meniscus 210 when the one end of the one side extension member 120 exposed through the lateral opening of the one side tunnel 310 and the other end of the other side extension member 130 exposed through the lateral opening of the other side tunnel 320 are pulled by predetermined force.

In addition, referring to FIG. 5, when the one side extension member 120 is inserted through the upper opening of the one side tunnel 310 and then the one end of the one side extension member 120 is moved to be exposed through the lateral opening of the one side tunnel 310, the intermediate support member 110 connected to the one side extension member 120 may be disposed to surround the meniscus 210, and the other side extension member 130 connected to the intermediate support member 110 may extend through the other side tunnel 310 such that the other end of the other side extension member 130 may be disposed to be exposed through the lateral opening of the other side tunnel 310.

As described above, the one side extension member 120 and the other side extension member 130 are fixed to the tibia 300, and thus the intermediate support member 110 may be fixed while surrounding the meniscus 210. Since the intermediate support member 110 is fixed and disposed as described above, it is possible to effectively prevent the meniscus from deviating from the exact position.

Figure 7:
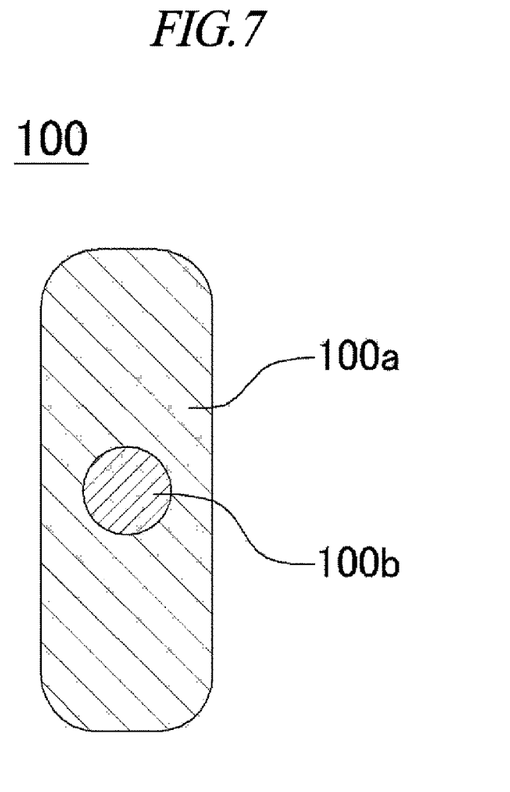
FIG. 7 is a view illustrating an example of a cross-sectional configuration of the device for supporting hoop stress applied to a meniscus and preventing deviation of the meniscus according to the exemplary embodiment of the present invention.

Meanwhile, FIG. 7 is a view illustrating an example of a cross-sectional configuration of the device for supporting hoop stress applied to a meniscus and preventing deviation of the meniscus according to the exemplary embodiment of the present invention.

According to the exemplary embodiment of the present invention, each of the intermediate support member 110, the one side extension member 120, and the other side extension member 130 may include a rigid member made of a rigid element having an elastic modulus of a predetermined level or higher. In addition, the intermediate support member 110, the one side extension member 120, and the other side extension member 130 may be provided as a one-piece member by being continuously connected to one another. Here, the rigid member having an elastic modulus of a predetermined level or higher means a member having an elastic modulus of a high level that may be considered and recognized as not being elastically deformed by maximum tension caused by hoop stress applied to the meniscus. In addition, the rigid member may refer to a member that may be understood as being typically rigid in the medical field. The elastic modulus of the rigid member may be 10 GPa or more. However, the rigid member refers to a member which is rigid against longitudinal elasticity (resilience), and the rigid member may have flexibility against warping (bending) so as to easily surround the meniscus.

The hoop stress may be constantly supported by the rigid member which has no resilience and a limitation in elastic deformation in the longitudinal direction as described above.

In the exemplary embodiment of the present invention, the rigid member may have resistance against the hoop stress. Since the rigid member serves to withstand hoop stress applied to the meniscus and fix the position of the meniscus, the rigid member may have tensile strength of a predetermined level or higher. For example, the rigid member may have tensile strength of 100 MPa or more.

In the exemplary embodiment of the present invention, the intermediate support member 110, the one side extension member 120, and the other side extension member 130 may include a material that does not cause an adverse after implantation. The device 100 for supporting hoop stress applied to a meniscus and preventing deviation of the meniscus is inserted and positioned into a knee joint, that is, a human body, and thus the intermediate support member 110, the one side extension member 120, and the other side extension member 130 may include a material that does not cause an adverse after implantation in a human body. More preferably, a surface of each of the intermediate support member 110, the one side extension member 120, and the other side extension member 130 may be made of a material that does not cause an adverse after implantation in a human body. In addition, the material may have no hygroscopicity so that the material does not absorb blood or the like in a human body. As an example, the intermediate support member 110, the one side extension member 120, and the other side extension member 130 may be made of a material including, but not limited only to, Gore-Tex resin, Teflon resin, Mersilene tapes, or the like.

According to the exemplary embodiment of the present invention, each of the intermediate support member 110, the one side extension member 120, and the other side extension member 130 may include the rigid member and an elastic member that has a smaller elastic modulus than the rigid member. In addition, the intermediate support member 110, the one side extension member 120, and the other side extension member 130 may be provided as a one-piece member by being continuously connected to one another. For example, in the one-piece member, the rigid member of the intermediate support member 110 may be continuously connected to the rigid member of the one side extension member 120 and the rigid member of the other side extension member 130, and the elastic member of the intermediate support member 110 may be continuously connected to the elastic member of the one side extension member 120 and the elastic member of the other side extension member 130. In addition, the elastic member may have an elastic modulus that may maintain the connection even though the rigid members are disconnected due to tension of a predetermined level or higher. In addition, the elastic member may have flexibility against warping (bending) so as to surround the meniscus.

Since the intermediate support member 110, the one side extension member 120, and the other side extension member 130 are combined to each have the rigid member and the elastic member as described above, the elastic members, which are tougher than the rigid members and have resilience, remain connected without being disconnected even though the rigid members, which consistently surround the meniscus and support the hoop stress without being deformed in the longitudinal direction, are disconnected (cut). At the ordinary time when the rigid members are not disconnected, most parts of tension caused by the applied hoop stress are applied to the rigid members having no resilience, and as a result, the tension is less applied to the elastic members relatively having resilience.

Since the elastic members are stretched relatively well even by low tension in comparison with the rigid members, the tension caused by hoop stress is less applied to the elastic members at the ordinary time, but the elastic members may support the entirety of the tension caused by hoop stress from the time when the rigid members are disconnected. That is, since the elastic member has a relatively small elastic modulus (high resilience) and extends together with the rigid member in the longitudinal direction, the elastic member is on standby without supporting the tension at the ordinary time when the rigid member is not disconnected, but the elastic member is somewhat stretched at last because of resilience relatively higher than resilience of the rigid member in an emergency in which the rigid member is disconnected. Therefore, the elastic member may serve as an assistive member that prepares for an emergency in which resistance against the tension is required. Therefore, the elastic member may secondarily support the meniscus by using somewhat high resilience even though the rigid member is unexpectedly disconnected.

FIG. 7 is a view illustrating an example of a cross-sectional configuration of the device for supporting hoop stress applied to a meniscus and preventing deviation of the meniscus according to the exemplary embodiment of the present invention.

According to the exemplary embodiment of the present invention, as illustrated in FIG. 7, a rigid member 100a may be provided to surround an elastic member 100b when viewed in a cross-sectional view. Since the elastic member 100b is provided in the form of a core with respect to the rigid member 100a, the disconnected or damaged rigid member 100a may be moved along the elastic member 100b, which is not yet disconnected, and then the rigid member 100a may be easily removed even though the rigid member 100a is unexpectedly disconnected. In addition, in the case in which the elastic member 100b is provided in the form of a core, the rigid member 100a, which is exposed to the outside, may be made of a material including one or more substances that have no hygroscopicity and cause no adverse after implantation.

As described above, since the elastic member, which is tougher than the rigid member and has higher resilience than the rigid member, is provided in the rigid member 100a, it is possible to prevent the entire disconnection of the device 100 for supporting hoop stress applied to a meniscus and preventing deviation of the meniscus even though the rigid member 100a included in the device 100 for supporting hoop stress applied to a meniscus and preventing deviation of the meniscus is disconnected.

In the exemplary embodiment of the present invention, as illustrated in FIGS. 4B and 7, the intermediate support member 110 has a height greater than a width in view of a cross section thereof, and a lateral surface of the intermediate support member 110, which corresponds to the height, may be in contact with an outer portion of an outer circumference of the meniscus. As an example, the intermediate support member 110 may have, but not limited only to, a cross-sectional height of 3 mm and a cross-sectional width of 1 mm. In addition, the height of the intermediate support member 110 may be smaller than a height at an outer side of the meniscus. Since the intermediate support member 110 has a cross-sectional shape having a height greater than a width and the lateral surface of the intermediate support member 110 is in contact with the joint capsule outside the meniscus 210 as described above, the intermediate support member 110 may be more stably and fixedly disposed with respect to the meniscus 210.

In addition, in the exemplary embodiment of the present invention, as illustrated in FIG. 5, the lateral opening of the one side tunnel 310 in the tibia 300 may be an opening identical to (coincident with or shared with) the lateral opening of the other side tunnel 320 in the tibia 300.

In addition, the one end of the one side extension member 120 and the other end of the other side extension member 130 may extend to the lateral surface of the tibia 300 through the identical opening and then may be fixed to the lateral surface of the tibia 300. To fix the one end of the one side extension member 120 and the other end of the other side extension member 130 to the lateral surface of the tibia 300, the device 100 for supporting hoop stress applied to a meniscus and preventing deviation of the meniscus may include a fixing unit 140 that fixes the one end of the one side extension member 120 and the other end of the other side extension member 130 to the lateral surface of the tibia 300. Here, the fixing unit 140 may be, but not limited only to, a screw.

In addition, although not clearly illustrated in the drawings, in the exemplary embodiment of the present invention, the one end of the one side extension member 120 may protrude through one side opening of the one side tunnel 310, and the other end of the other side extension member 130 may protrude through the other side opening of the other side tunnel 320 which is distinguished from the one side opening. In a case in which the one side opening and the other side opening are not coincident with each other but the one side opening and the other side opening are provided separately from each other, the one end of the one side extension member 120 and the other end of the other side extension member 130 may be separately fixed.

Meanwhile, a method of supporting hoop stress applied to a meniscus and preventing deviation of the meniscus and a robot (surgical device) according to the exemplary embodiment of the present invention will be described below. However, the method of supporting hoop stress applied to a meniscus and preventing deviation of the meniscus and the robot (surgical device) according to the present invention are implemented by using the above-mentioned device for supporting hoop stress applied to a meniscus and preventing deviation of the meniscus according to the present invention, and the method, the robot, and the device are different from one another only in terms of Title of Invention and categories but share the identical or corresponding technical spirit, and therefore, the constituent elements identical or similar to the above-mentioned constituent elements will be assigned with the same reference numerals, and the repetitive description thereof will be briefly described or omitted.

A second aspect of the present invention provides the method of supporting hoop stress applied to a meniscus and preventing deviation of the meniscus, the method including: a step S100 of forming, by a surgical device, the one side tunnel 310 and the other side tunnel 320 in the tibia 300; a step S200 of disposing, by the surgical device, the device 100 for supporting hoop stress applied to the meniscus and preventing deviation of the meniscus so that the intermediate support member 110 surrounds the meniscus 210, the one end of the one side extension member 120 extends to the lateral surface of the tibia 300 through the lateral opening of the one side tunnel 310, and the other end of the other side extension member 130 extends to the lateral surface of the tibia 300 through the lateral opening of the other side tunnel 320; and a step S500 of fixing, by the surgical device, the one end of the one side extension member 120 and the other end of the other side extension member 130 to the lateral surface of the tibia 300.

In the step S300 in the exemplary embodiment of the present invention, the surgical device moves the one end of the one side extension member 120 so that the one end of the one side extension member 120 passes alternately through the inner and outer portions of the joint capsule outside the meniscus 300 at least once, the surgical device moves the one end of the one side extension member 120 so that the one end of the one side extension member 120 moves out of the meniscus 300, and thus the surgical device may allow the intermediate support member 110 to pass alternately through the inner and outer portions of the joint capsule outside the meniscus 300 at least once.

As an example, the surgical device may be a robot for performing a surgical operation. The robot may include a robot arm and a control unit for controlling the robot arm in order to perform the method of preventing deviation of the meniscus. The robot for performing a surgical operation may include various constituent elements apparent to those skilled in the art in addition to the above-mentioned constituent elements, and a detailed description thereof will be omitted.

That is, a third aspect of the present invention may provide a robot which is configured to prevent deviation a meniscus and includes a robot arm, and a control unit which controls the robot arm to form the one side tunnel 310 and the other side tunnel 320 in the tibia 300, controls the robot arm to dispose the device 100 for supporting hoop stress applied to the meniscus and preventing deviation of the meniscus so that the intermediate support member 110 surrounds the meniscus 210, the one end of the one side extension member 120 extends to the lateral surface of the tibia 300 through the lateral opening of the one side tunnel 310, and the other end of the other side extension member 130 extends to the lateral surface of the tibia 300 through the lateral opening of the other side tunnel 320, and controls the robot arm to fix the one end of the one side extension member 120 and the other end of the other side extension member 130 to the lateral surface of the tibia 300.

In addition, a practitioner (person), instead of the robot, may perform the method of preventing deviation of a meniscus as necessary in consideration of a surgical environment or the like. In the case in which the practitioner, instead of the robot, performs the method of preventing deviation of a meniscus as described above, the practitioner may prepare typical surgical tools corresponding to the respective steps S100, S300, and S500 in order to appropriately and effectively perform the method of preventing deviation of a meniscus.

In addition, the above-mentioned method of preventing deviation of a meniscus according to the second aspect of the present invention may be implemented as applications or may be in the form of program instructions executable through various computer elements, and then written in a computer-readable recording medium. The computer-readable recording medium may include program instructions, data files, data structures, or the like, in a stand-alone form or in a combination thereof.

The program instructions stored in the computer-readable recording medium may be designed and configured specifically for the present invention or may be publicly known and available to those skilled in the field of computer software.

Examples of the computer-readable recording medium may include magnetic media, such as a hard disk, a floppy disk and a magnetic tape, optical media, such as CD-ROM and DVD, magneto-optical media, such as a floptical disk, and hardware devices, such as ROM, RAM and flash memory, which are specifically configured to store and run program instructions.

Examples of the program instructions may include machine codes made by, for example, a compiler, as well as high-language codes that may be executed by an electronic data processing device, for example, a computer, by using an interpreter. The above hardware devices may be configured to operate as one or more software modules in order to perform the operation of the present invention, and the opposite is also possible.

It will be appreciated that the exemplary embodiments of the present invention have been described above for purposes of illustration, and those skilled in the art may understand that the present invention may be easily modified in other specific forms without changing the technical spirit or the essential features of the present invention. Therefore, it should be understood that the above-described exemplary embodiments are illustrative in all aspects and do not limit the present invention. For example, each component described as a single type may be carried out in a distributed manner. Likewise, components described as a distributed type can be carried out in a combined type.

The scope of the present invention is represented by the claims to be described below rather than the detailed description, and it should be interpreted that the meaning and scope of the claims and all the changes or modified forms derived from the equivalent concepts thereto fall within the scope of the present invention.

The invention claimed is:

1. A method of supporting hoop stress applied to a meniscus and preventing deviation of the meniscus, the method comprising:
   (a) providing a device comprising an intermediate support member having a first end and a second end, a first extension member connected to the first end of the intermediate support, and a second extension member connected to the second end of the intermediate support;
   (b) forming, by a surgical device, a first tunnel and a second tunnel in tibia, said first tunnel and said second tunnel each having a first opening on upper surface of the tibia and a second opening on lateral surface of the tibia;
   (c) disposing, by the surgical device, the device so that the intermediate support member surrounds the meniscus, end of the first extension member extends through the first tunnel from the first opening of the first tunnel to the second opening of the first tunnel, and end of the second extension member extends through the second tunnel from the first opening of the second tunnel to the second opening of the second tunnel; and
   (c) fixing, by the surgical device, the end of the first extension member and the end of the second extension member to the lateral surface of the tibia at the second opening of the first tunnel and the second tunnel,
   wherein, in step (b), the surgical device moves the end of the first extension member so that the intermediate support member pass alternately through inner and outer portions of joint capsule outside the meniscus at least once.

2. The method of claim 1, wherein the intermediate support member, the first extension member, and the second extension member are continuously connected to one another and include a rigid member having an elastic modulus of 10 GPa or more.

3. The method of claim 2, wherein the intermediate support member, the first extension member, and the second extension member are continuously connected to one another and further include an elastic member having an elastic modulus smaller than an elastic modulus of the rigid member.

4. The device of claim 3, wherein the elastic member maintains the connection when the rigid member is disconnected.

5. The method of claim 3, wherein the rigid member is provided to surround the elastic member.

6. The method of claim 1, wherein the intermediate support member has a height greater than a width in view of a cross section thereof, and a lateral surface of the intermediate support member, which corresponds to the height, is in contact with a joint capsule outside the meniscus.

7. The method of claim 1, wherein the intermediate support member, the first extension member, and the second extension member include a biocompatible material.

8. The method of claim 1, wherein the first opening of the first tunnel is formed adjacent to one end of the meniscus, and the first opening of the second tunnel is formed adjacent to the other end of the meniscus.

9. The method of claim 1, wherein the second opening of the first tunnel and the second opening of the second tunnel form a single opening.

10. The method of claim 9, wherein the end of the first extension member and the end of the second extension member extend to the lateral surface of the tibia through the single opening and are fixed to the lateral surface of the tibia.

11. The method of claim 9, further comprising a step of providing a fixing unit on the lateral surface of the tibia wherein the end of the first extension member and the end of the second extension member are fixed to the fixing unit.

12. The method of claim 11, wherein the fixing unit is a single fixing unit and wherein both of the end of the first extension member and the end of the second extension member are fixed to the single fixing unit.

* * * * *